United States Patent [19]

Dooley et al.

[11] 4,036,050
[45] July 19, 1977

[54] ENGINE MONITORING APPARATUS

[76] Inventors: Joseph L. Dooley, 2753 W. 84th St., Chicago, Ill. 60652; Edward Yelke, 945 S. Kensington Ave., LaGrange, Ill. 60525

[21] Appl. No.: 670,058

[22] Filed: Mar. 24, 1976

[51] Int. Cl.² .......................................... G01M 15/00
[52] U.S. Cl. ..................................... 73/119 A; 73/115
[58] Field of Search ................. 73/119 A, 115, 398 R

[56] References Cited
U.S. PATENT DOCUMENTS

| | | | |
|---|---|---|---|
| 3,371,525 | 3/1968 | Mitchell | 73/115 |
| 3,874,225 | 4/1975 | Fegel | 73/119 A X |

*Primary Examiner*—Jerry W. Myracle
*Attorney, Agent, or Firm*—Neuman, Williams, Anderson & Olson

[57] ABSTRACT

Engine monitoring apparatus is disclosed in which the cylinder pressure changes in a fuel injected engine are monitored through the use of a transducer device which produces an electrical signal responsive to pressures exerted on an injector nozzle from within the cylinder. The transducer is mounted to the nozzle holding brackets or fasteners which act to maintain pressure tending to seat the nozzle against an inlet port in the cylinder and, as such, is responsive to axial pressures exerted on the nozzle assembly from within the cylinder. Methods and apparatus for mounting the transducer device to the holding brackets of various types of nozzle assemblies are disclosed along with read-out devices including a tachometer circuit for utilizing the transducer output signal for performance monitoring and diagnostic applications.

10 Claims, 12 Drawing Figures

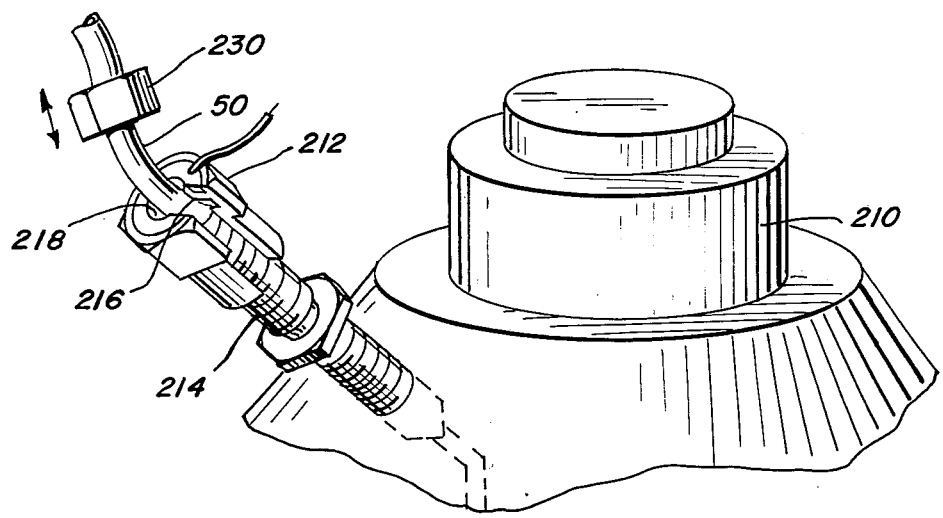
FIG. 8
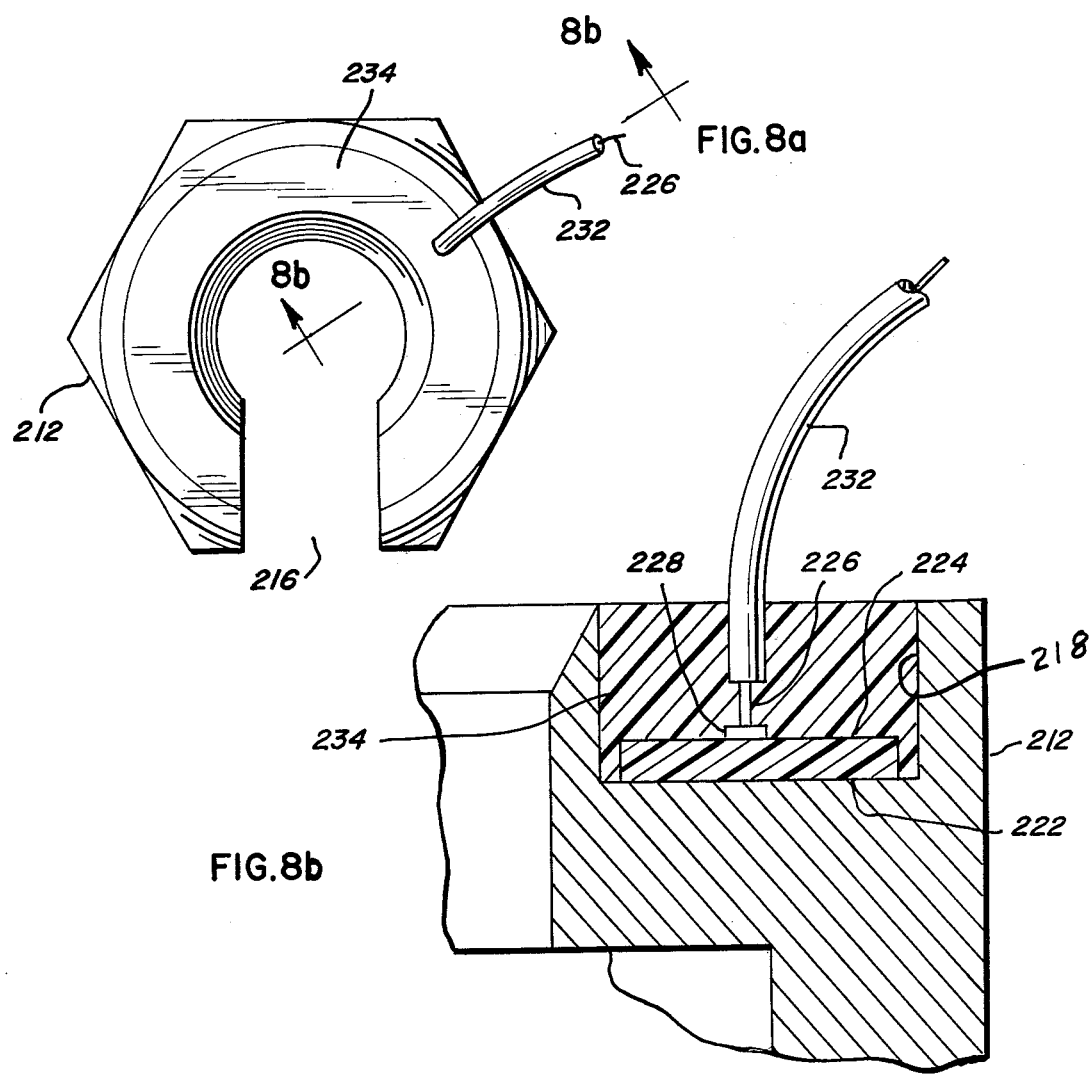
FIG. 8a
FIG. 8b

ENGINE MONITORING APPARATUS

FIELD OF THE INVENTION

This invention relates generally to performance monitoring devices for internal combustion engines and more particularly to instruments for sensing and utilizing the pressure developed within an engine cylinder.

BACKGROUND OF THE INVENTION

Devices for monitoring the performance of internal combustion engines have proliferated in recent years as the need for greater performance, fuel economy and pollution control with such engines has increased. For years a wide variety of transducers have been used for measuring water temperature, oil pressure and temperature, manifold vacuum and engine speed. Numerous other engine parameters, such as timing, dwell angle, and other characteristics have been detected through measurements taken from the engine electrical system. However, performance monitoring systems developed thus far have largely been limited to use in measuring parameters which are detectable through the drive train or from external or bolt-on equipment such as the distributor, the carburetor, the vacuum, fuel and cooling system lines, the radiator or the electrical system. For numerous performance monitoring applications, and in particular for engine diagnostic instruments it is highly desirable to obtain an indication of the performance of the engine internally. The present invention satisfies this need for internal performance monitoring in that it provides for measurements of the pressure developed within the cylinder itself in an economical and universally applicable manner.

Diesel engines, in particular, pose problems from a performance monitoring or diagnostic standpoint in that the conventional spark distribution system, a convenient source of timing and speed signals, is either not present or is rendered inoperative during normal operation. Monitoring devices relying on speed-related signals, such as a tachometer, assume an added degree of complication and expense in the absence of an electrical distributor system. While signals representing engine speed can be taken from transducers on the flywheel or dynamic damper, the infinite number of damper gear ratios found on different engine models has impeded the development of a truly universal flywheel pick-up system. Speed-related signals have also been taken from engine alternators, but the output on such devices is dependent on the voltage regulator and requires amplification for low charging conditions. Speed-related signals can also be developed from the belts, pulleys, timing chains and other mechanical engine components, but most of these devices are either inaccessible from a practical standpoint or vary with the make and model of the engine and as such do not lend themselves to universal application with monitoring equipment.

Systems have been devised by others which utilize the sequential performance of the fuel-injection pump or lines for developing signals useful in engine timing. For example, U.S. Pat. No. 3,511,088 of Preston R. Weaver discloses a system wherein a piezoelectric quartz pressure transducer is adapted for coupling to a fuel line so as to provide an output signal which varies with the radial expansion resulting from increased pressure within the fuel line. While the arrangement disclosed in the aforesaid patent may provide a general indication of changes in line pressure, it is of no value in analysis of the combustion process within the cylinder itself in that the fuel line is isolated from the combustion chamber or cylinder much of the time by pressure regulating springs and valves within the injector nozzle assembly. In addition, the aforesaid system requires various electrical and mechanical damping components for reducing the effects of engine and fuel line vibration on the transducer output signal.

Piezoelectric transducers have also been used in laboratory-type cylinder pressure gauges wherein the quartz material is housed in a special transducer fitting which is tapped through the engine housing into the proximity of the walls of the cylinder combustion chamber. Devices of this type are described in "Diesel and High Compression Gas Engines" 3rd Ed. 1974 by Kates and Luck, Chapter 17. However, such devices rely on stress detected through the cylinder walls and require either specially casted engine housings or engine housing modifications which make them impractical for widespread use as diagnostic devices outside the laboratory.

SUMMARY OF THE INVENTION

The monitoring system of the present invention overcomes the limitations inherent in the aforesaid prior art devices. The method and apparatus herein set forth provides a representation of pressure changes within the cylinder of a fuel injected engine without elaborate modification of existing engine components. Specifically, a sensitive stress responsive material such as a piezoelectric slab or plate is mounted to specific stress points on the brackets or fasteners which maintain the injector nozzle assembly pressure seated against an inlet port of the cylinder. Pressure developed within the cylinder acts on the nozzle surfaces in the vicinity of the fuel inlet port and is transmitted axially along the nozzle assembly to the stress transducer through the bracket or other nozzle holding means. Because the nozzle assembly, its holding bracket and the transducer are all fastened to the engine housing in a semi-rigid fashion and because of the frequency response characteristics of the transducer itself, an accurate representation of cylinder pressure variations is provided by the transducer output signal without any appreciable distortion resulting from engine vibration. The output signal is of such a quality that it may be used to drive an integrating tachometer circuit to provide an indication of engine speed or, in the alternative, it may be viewed on a CRT display or processed in a variety of circuits to provide detailed information, such as compression, peak firing pressure, horsepower, the injector nozzle condition, etc., indicating internal engine performance.

Other features and advantages of the invention will become apparent upon reading the following detailed description and upon reference to the drawings.

BRIEF DESCRIPTION OF THE DRAWINGS

FIG. 8 is a perspective view of a portion of an injection pump with a transducer device attached.

FIGS. 8(a) and 8 (b) are detailed plan and cross sectional veiws, respectively, of the transducer device of FIG. 8.

DESCRIPTION OF THE ILLUSTRATED EMBODIMENTS

Figure 1:
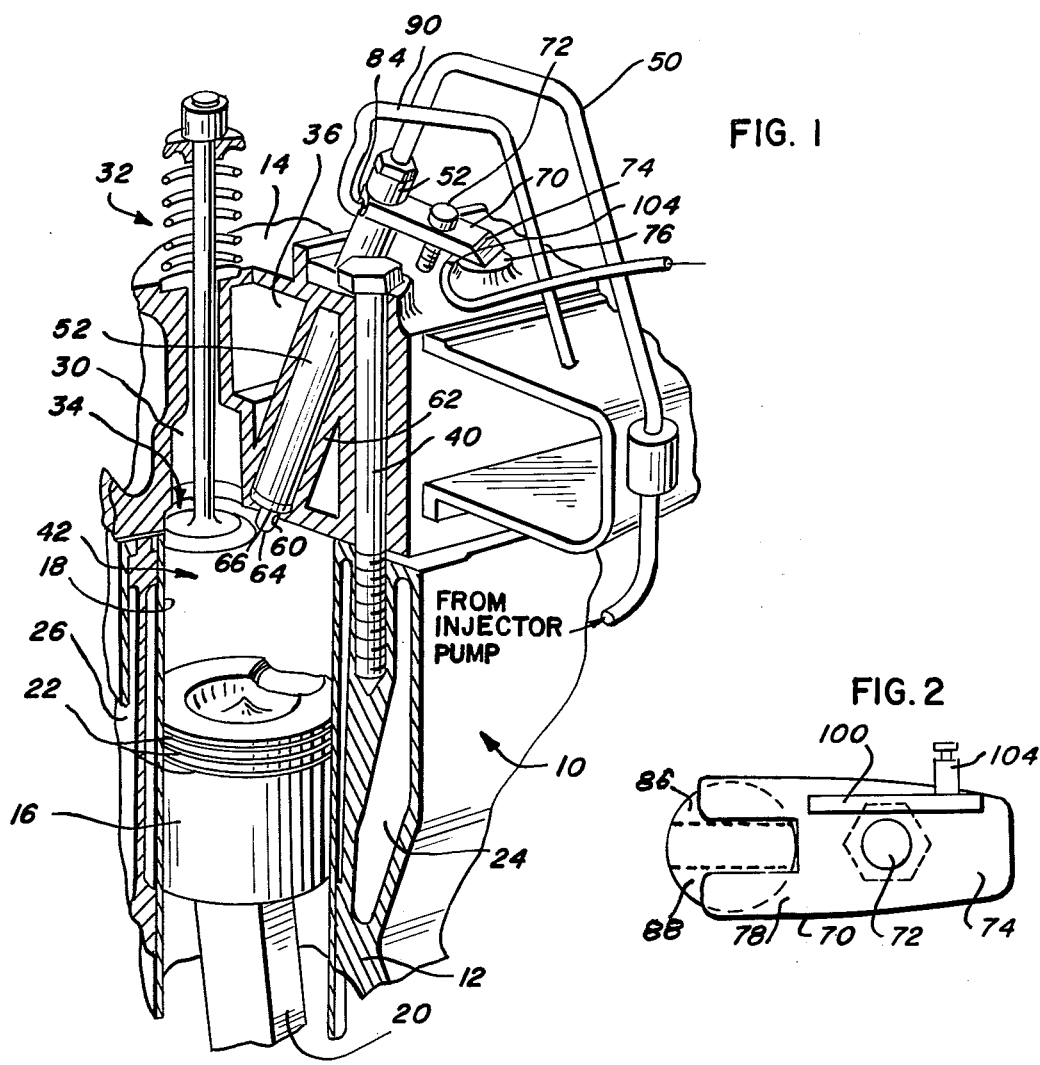
FIG. 1 is a perspective cut-away view of a portion of a diesel engine to which the monitoring system of the present invention is applicable.

Turning first to FIG, 1, there is shown a section of a typical diesel engine having a housing 10 which consists generally of a block assembly 12 and compression head 14. The block is shown cut away to reveal a piston 16 which operates within a cylinder 18. The piston is coupled to a crankshaft (not shown) via a connecting rod 20 and has a plurality of rings 22 which operate in a conventional manner to maintain compression and enhance lubrication within the cylinder 18. Passages 24, 26 are provided for coolant flow.

The compression head 14 includes an air intake chamber 30 which provides air for the combustion process through the operation of a conventional valve mechanism 32 which opens and closes an air inlet port 34 under the control of appropriate linkage driven by other components of the engine. The compression head 14 also houses a passage 36 for water or coolant flow to control the temperatures developed within the compression head. Appropriate head bolts 40 and gaskets couple the head 14 to the block assembly 12 in an airtight seal to define a combustion chamber 42 which expands and contracts in volume with movement of the piston 16 within the cylinder 18.

Fuel is provided to the combustion chamber of each cylinder by a fuel injector pump (not shown) through a fuel line 50 and nozzle assembly 52. Several different injector systems are employed with diesel engines. Typically, a single injector pump with appropriate fluid gates provides fuel for each of the cylinders in a cyclical fashion. In some engines, however, each cylinder is provided with a separate pump which may be either remote from or integral with the nozzle assembly 52. It is also common to use a plurality of nozzle assemblies for injecting fuel into a given cylinder or a single nozzle assembly with a plurality of orifices for distributing fuel within the combustion chamber 42. The apparatus of the present invention, as defined below, is applicable to any and all of the aforesaid configurations.

The nozzle assembly 52 carries fuel from the line 50 to an inlet port 60 in the cylinder 18. An appropriate passage or sleeve 62 is cast or otherwise provided through the coolant passage 36 of the engine housing to prevent leakage of coolant to the outside of the engine or into the cylinder 18. At the fuel inlet port 60 into the cylinder 18 is an injector gasket 64, typically in the form of a copper or brass washer surrounding a protruding portion or orifice 66 at the tip of the nozzle assembly 52.

Figure 2:
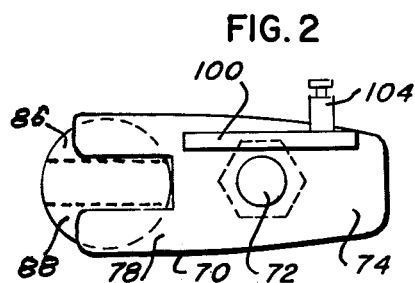
FIG. 2 is a plan view of the underside of the nozzle holding dog of the diesel engine of FIG. 1 showing a piezoelectric transducer attached thereto.

For the purpose of seating the nozzle assembly 52 in sealing engagement with the cylinder inlet port 60 there is provided holding means fastened to the engine housing and adapted for engaging the nozzle assembly 52 and maintaining axial pressure thereon toward the engine housing. To this end, there is depicted in the embodiment of FIG. 1 and in the more detailed view of FIG. 2 a lever-type member or dog 70 which is coupled to the engine housing 10 by a fastening means in the form of a bolt or screw 72 which extends through a hole in the dog. The dog 70 has one end 74 which abuts against a raised portion 76 formed on the compression head 14. The other end 78 of the dog 70 is of a generally U-shaped configuration for partially surrounding and engaging recessed portions 84 formed on the periphery of the nozzle assembly 52 at a point external to and spaced from the engine housing 10. This recessed portion of the assembly 52 includes a pair of shoulders 86, 88 against which the U-shaped end 78 of the dog 70 exerts pressure under the cantilever action developed by the fastener 72 upon tightening thereof.

The nozzle assembly 52 may be any of a variety of different types. Typically, injector nozzles include an internal spring-loaded valve which is hydraulically opened by the fuel provided by the pump as the pressure exerted by that fuel exceeds a predetermined minimum level. As such, the nozzle assembly isolates the injector line 50 from pressures created in the combustion chamber 42 during most of the combustion cycle. Although not relevant to the present invention, it is noted that most injector nozzles additionally provide a metering function in that the volume of fuel for a given injection cycle is carefully controlled and excess fuel supplied by the pump is bypassed back to the fuel supply through a return line 90 shown in FIG. 1.

In normal operation of the diesel described, air supplied to the cylinder 18 through the valve port 34 is compressed during upward movement of the piston 16. After closure of the port 34 but while compression is still increasing within the cylinder 18, the injector pump supplies fuel to the line 50. When the pressure of the fuel within the line 50 is sufficient to open the spring-loaded valve in the nozzle assembly 52 ejection into the cylinder 18 begins. The combination of heat and pressure within the combustion chamber 42 expands and ignites the fuel, resulting in a still further and more rapid increase in pressure to begin the power stroke which forces the piston 16 downward in the cylinder 18.

In accordance with the present invention, means are provided to monitor these pressure changes within the combustion chamber 42 so as to provide an electrical signal which is useful in monitoring engine performance or performance within the individual cylinder. More specifically, a transducer device of appropriate sensitivity is coupled to the bracket and fastener assembly holding the nozzle seated into its cylinder inlet port. Axial forces on the nozzle assembly created by pressure changes within the combustion chamber 42 are thereby detected external to the engine housing to facilitate convenient and economical performance monitoring. To these ends, the embodiment depicted in FIGS. 1 and 2 includes a stress transducer 100 shown mounted to the underside of the lever-type member or dog 70 at or near a point of flexing which, in this instance, is adjacent the pivot point at the fastener 72.

Figure 5:
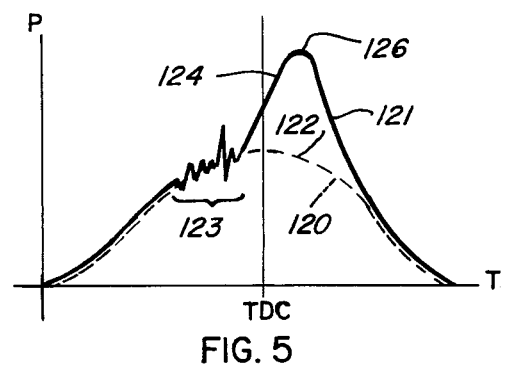
FIG. 5 is a view of the signal developed on the CRT display of FIG. 3 by the transducer apparatus of the present invention during the performance cycle of a typical diesel engine.

The transducer 100 is typically a ceramic crystal structure possessing piezoelectric properties, i.e., the ability to produce a voltage when subjected to a mechanical stress acting in a specific orientation with respect to the crystallographic axis of the material. Materials such as Mallory P.C. 5 or Clevite P.Z.T. 5 have proven suitable for this purpose. Typical materials of this type have two parallel major surfaces between which the stress-responsive voltage is developed. In the embodiment shown in FIG. 2, one of these surfaces is bonded by a conductive adhesive to the metal bracket or dog 70, while the other surface is electrically coupled to an output terminal 104 for connection to monitoring apparatus to be described below. The adhesive bonding the transducer 100 to the dog 70 is preferably of a type which maintains electrical contact between the transducer 100 and the dog 70 through the wide variations of temperature encountered during normal operation of the engine. Mounted on the dog 70 as described, the transducer 100 is flexed or bent as a result of axial pressures acting along the body of the nozzle assembly 52 during pressure changes within the combustion chamber 42. At the same time, pressures exerted radially from within the fuel line 50 or nozzle assembly 52 have little or no effect on the transducer 100. Likewise, vibration from the engine itself has been found to have little or no effect on the signal developed by the transducer. In other words, the output voltage developed at the terminal 104, as shown in FIG. 5, is closely representative of actual cylinder pressure. A detailed discussion of this signal is presented below.

Figure 3:
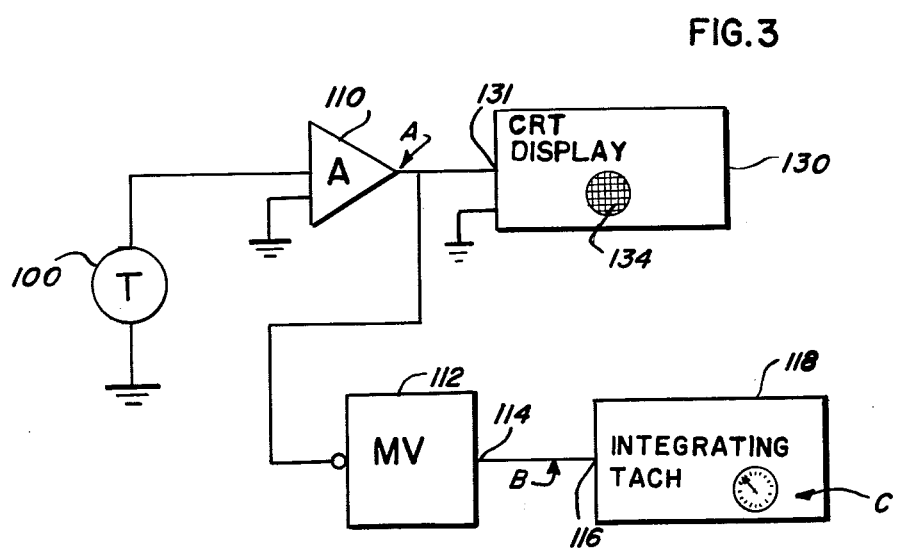
FIG. 3 is a block diagram of monitoring apparatus for use with the transducer arrangement shown in FIGS. 1 and 2.
Figure 4:
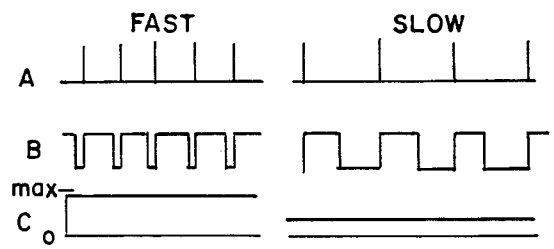
FIG. 4 is a timing diagram showing representative signals developed within the tachometer circuit of FIG. 3.

For the purpose of utilizing the transducer output signal to provide a visual indication of engine performance, various output devices may be provided. Two such devices, namely a tachometer circuit and a CRT display, are shown in FIG. 3. Turning first to the tachometer circuit, the transducer 100 provides an output pulse at its terminal 104 during each power cycle of the engine. While the transducer output is depicted herein as a voltage variation with respect to engine ground, it will be appreciated that a separate lead may, in some applications, be bonded to each surface of the transducer material and appropriate insulation provided to electrically isolate both surfaces of the piezoelectric material from the metal engine components. Because a piezoelectric transducer is sensitive to loading, an isolation amplifier 110 having a high-impedance input is provided to receive the signal from the transducer. In order to provide an output pulse of constant time duration in response to each of the transducer pulses, a timing circuit or multivibrator 112 is coupled to the output of the amplifier 110. The timing circuit 112, in turn, provides its output signal at a terminal 114 which is coupled to an input terminal 116 of an integrating tachometer 118. The signals A, B and C of FIG. 4 depict generally the voltages developed at the points A, B and C of FIG. 3, although the amplitude of the signal designated C may also be viewed as representative of the visual meter reading on the tachometer 118, since many simple tachometers mechanically integrate the input pulse train B without conversion to an intermediate D.C. signal. In conventional manner, the tachometer 118 effectively measures the D.C. content of the multivibrator output signal B to provide an output signal or reading C proportional to engine speed.

The tachometer circuit described above and various other monitoring devices are only dependent upon the existence of a recurring speed-related pulse such as that provided by the transducer 100. For other applications, and in particular for diagnosing problems arising within the cylinder, the pressure-time characteristic during the power cycle of the individual cylinder is of interest. The transducer apparatus of the present invention is of particular value for these more demanding monitoring applications. To this end the circuit of FIG. 3 is shown with an alternate output indicator in the form of a CRT display 130 having an input 131 coupled to receive the output of the isolation amplifier 110 for display on a screen 134. The display 130 may be a standard oscilloscope or any other display having a capability to synchronize automatically to the time base of the inut signal. Alternately the display may have its horizontal sweep triggered from or synchronized to an externally developed signal such as may be derived from a flywheel pick-up or from various timing pulses existing within the transducer output signal itself. The signal appearing on the screen 134 during monitoring of a properly operating cylinder is shown in the pressure-time trace of FIG. 5, wherein the voltage developed from the transducer 100 is the ordinate and time is the abscissa. A grid impressed on the screen 134 provides proper calibration. The amplitude of the signal at any given point above the zero axis represents instantaneous pressure within the cylinder. This amplitude can be compared against known standards to ascertain the performance of rings and valves in maintaining compression.

The pressure-time curves shown in FIG. 5 represent performance of the same cylinder under two separate conditions. The broken line or curve 120 represents the signal monitored on the screen 134 during operation of the cylinder with the fuel source to the cylinder interrupted, while the solid line or curve 121 represents the signal monitored on the screen 134 with the fuel injection system for the cylinder operative. From the broken-line trace 120 it is seen that during interruption of the fuel source to the cylinder the transducer 100 develops a signal, viewable on the screen 134, which represents the pressure change within the combustion chamber 42 (FIG. 1) resulting only from the contraction and expansion of the volume of the chamber 42 during one cycle of the piston 18. The point at which the piston achieves the position of top dead center (TDC) can be seen to occur when the pressure is at its highest point, as indicated at 122 in FIG. 5. For timing purposes the point TDC has substantial significance.

When the fuel injection system is operative a substantially different signal is developed by the transducer 100 and viewable on the screen 134. The trace or curve 121 rises similar to the curve 120 during upward travel of the piston 18 and before fuel injection. A high frequency oscillation, indicated at 123, occurs as a result of chatter in the injection nozzle during the fuel injection period. Absence of this chatter is an indication of a faulty nozzle. Observance of a change in these oscillations or a shift in time of these oscillations with respect to the time of TDC is also indicative of a faulty nozzle. Fuel is injected into the cylinder, the amplitude of the pressure-time curve increases rapidly, as shown at 124, until peak firing pressure occurs at point 126. If an injector nozzle is leaking or opening at insufficient pressure or has a clogged orifice, the amplitude of the transducer signal is reduced substantially from the norm to indicate a pressure only slightlyl higher than the cylinder pressure without injection.

While the aforesaid amplitude variations are of significant interest in and of themselves, the relationship between these variations on the time scale is of additional and potentially greater significance. For a given engine operating at a given speed, the time (commonly called "port closure") at which the injection pump (not shown) begins to deliver to the line 50 bears a fixed relationship to the time at which the piston 16 attains its top dead center (TDC) position.

Still further information can be obtained by providing each of the cylinders of an engine with a separate transducer and by viewing the output signals from each cylinder on separate traces of a single scope using a common time base synchronized to the signal from any one of the cylinders. Relative timing and amplitude information for each signal may be viewed on the screen to give a valuable indication of trouble spots or excessive wear in one or more cylinders which might result in deteriorating performance from the engine as a whole.

Figure 6A:
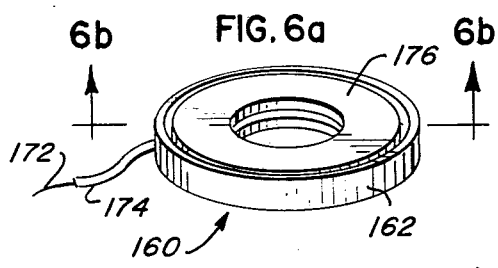
FIG. 6a is a perspective view of a transducer device suitable for use with bolt-on nozzle assemblies.
Figure 6B:
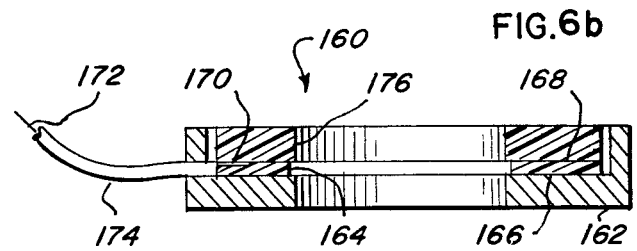
FIG. 6b is a cross-sectional view of the transducer device of FIG. 6a taken along the line A—A.
Figure 6:
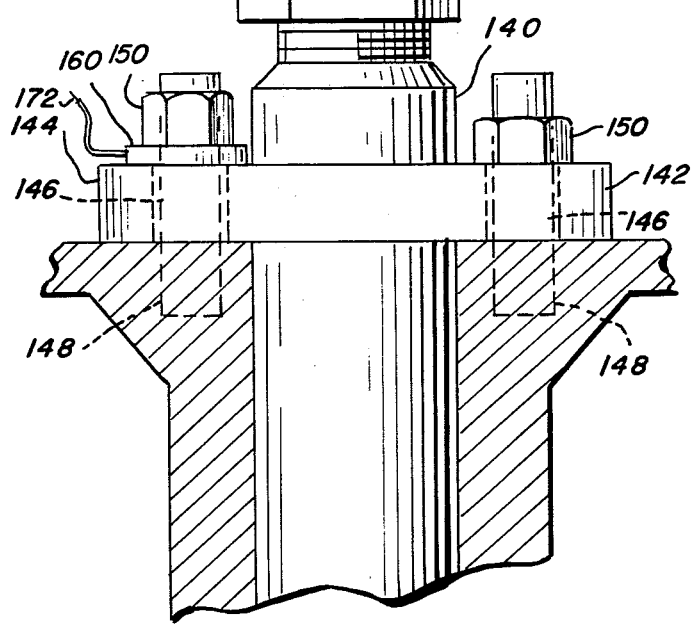
FIG. 6 is a plan view, partially in cross section, depicting the transducer apparatus of the present invention adapted to an alternate form of injector nozzle and holding means.

An alternate form of nozzle holding apparatus is shown in FIG. 6. A nozzle housing 140 has flanges 142, 144 protruding laterally therefrom. Each of the flanges 142, 144 has a hole 146 therethrough through which a stud 148 from the engine housing protrudes. The stud 148 is threaded to accept a nut 150 which acts upon the flange 142 to hold the nozzle assembly 140 into engagement with a cylinder inlet port (not shown) in a manner functionally identical to that described above for the nozzle assembly of FIG. 1.

In keeping with the principles of the present invention, the nozzle holding means shown in FIG. 6 has associated therewith a washer-type transducer structure 160 which is compressed between one of the stud nuts 150 and the holding bracket or flange 144 so as to be compressed in response to pressures exerted axially along the nozzle assembly 140 from within the combustion chamber 42 (FIG. 1). As shown in the more detailed views of FIGS. 6 and 6a, the transducer device 160 is of sandwich-type construction and includes an outer disc 162 of electrically conductive metal having a cavity therein which houses a thin disc 164 of piezoelectric material, the lower surface 166 of which is bonded to the conductive housing 162 by a suitable conductive adhesive having high temperature-resistant properties. The opposite surface 168 of the piezoelectric disc has an electrical contact 170 soldered thereto which is coupled through a wire 172 extending through the outer disc 162 in an insulator 174. To complete the sandwich, a second disc 176 is inserted over the upper surface 168 of the piezoelectric material 164. The disc 176 can be made of insulating dielectric materials so as to maintain the electrical isolation which must exist between the surfaces 166, 168 of the piezoelectric material 164 or, in the alternative, the disc may be of metal material and separated from the surface 168 of the piezoelectric disc by a suitable insulating washer or disc (not shown).

When the transducer structure 160 is secured between the holding nut 150 and the bracket or flange 144 of the nozzle assembly 140, forces acting axially on the nozzle compress or relax the piezoelectric material 164 so as to develop a voltage change between the upper and lower surfaces 168, 166 respectively. As with the transducer 100 shown in FIGS. 1 and 2, the engine assembly itself acts as a ground terminal for the signal developed across the transducer, and the single lead 172 carries the signal to appropriate monitoring apparatus, such as that shown in FIG. 3 and discussed above.

From the foregoing description, it is seen that the washer-type transducer assembly 160 can be used in association with any injector nozzle which is secured to the engine housing by bolts, screws, or any other circular or cylindrical fastener. For example, the washer transducer 160 could be used with the fastener 72 to hold the dog 70 of the nozzle holding apparatus shown in FIGS. 1 and 2 in place of the elongated transducer 100 shown in FIG. 2. Appropriately enlarged, the transducer structure 160 can also be readily adapted to fit over a screw-in type injector nozzle of the type which is threaded into the engine housing or otherwise secured to the housing by screw-type fittings which are coaxial with the nozzle itself.

Figure 7:
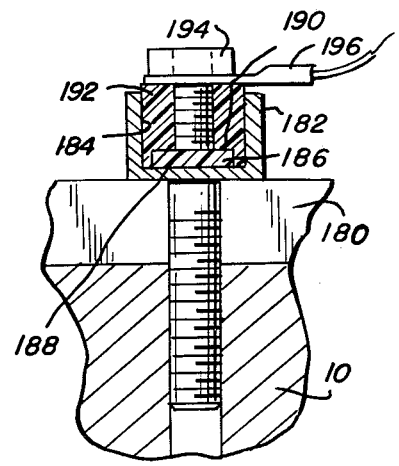
FIG. 7 is a cross-sectional view of still a further embodiment of the transducer assembly of the present invention.

A still further embodiment of the transducer assembly of the present invention is shown in FIG. 7, wherein the injector nozzle holding bracket or flange 180 is secured to the engine housing 10 by a bolt-type fastener 182. The fastener 182 contains a cavity 184 which houses a disc 186 of piezoelectric material of the type described above. One surface 188 of the material 186 is bonded to the fastener 182 by suitable conductive adhesive having high-temperature-resistant characteristics. The other surface 190 of the material 186 is insulated from the fastener housing 182 by a suitable dielectric insert or plug 192. Inserted into the plug 192 is a bolt or screw 194 which extends axially into engagement with the surface 190 of the piezoelectric material 186 to form a conductive path therewith. A suitable connector 196 takes the transducer signal from the bolt or screw 194 for connection to suitable monitoring apparatus such as that described above with respect to FIGS. 3-5. The bolt-type transducer shown in FIG. 7, like the washer-transducer shown in FIG. 6, is adaptable to a variety of nozzle holding applications and could, for instnce, act as a replacement for the fastener 72 in the apparatus shown in FIG. 1 or as a replacement for the stud and nut 148, 150 with the injector nozzle depicted in FIG. 6.

Still further information concerning the performance of an engine cylinder can be obtained by monitoring the operation of the fuel distribution system that delivers fuel through the line 15 to the nozzle assembly 52. Information concerning the timing and volume of fuel flow can be useful in several important ways in engine diagnosis, as set forth in the aforesaid Weaver U.S. Pat. No. 3,511,088. The repetitive pulsating character of fuel flow within the injector line may be sensed to develop a signal for driving a tachometer circuit such as that shown in FIG. 3 or for monitoring the timing of fuel injection relative to other activity occurring within the operating cycle of a given cylinder. Given an appropriate dual-trace display, the injection of fuel into the line 50 can be viewed simultaneously with the cylinder pressure signal discussed above and the relative timing between events occurring within the fuel injection system and within the combustion chamber 42 can be studied. While others have disclosed transducers for monitoring the fuel flow in the injector system, this apparatus has been somewhat costly, complicated, and limited in applicability to existing injector systems.

In keeping with the principles of the present invention, there is shown in FIGS. 8, 8a and 8b a simple, economical transducer for monitoring axial forces developed within the fuel line 50 by the injector pump 210. The transducer is housed in a split nut 212, which is similar to conventional nuts of the type used for holding fuel lines in sealing engagement with high pressure fittings such as the discharge outlet 214 shown in FIG. 8. The principal difference between the nut 212 and a conventional nut is that the nut 212 is cut away in an axial area 216 for ease of insertion onto the line 50 and is adapted to house a stress responsive material in a cavity 218 formed therein. As shown in more detail in FIGS. 8a and 8b, the stress responsive material, typically a slab or plate of piezoelectric material, is in the form of a washer-type insert 220 having one surface or face 222 thereof bonded to the metal surface of the nut 212 by a suitable epoxy which maintains conduction between the insert 220 and the nut through wide variations of temperature. An opposite face 224 of the insert 220 is insulated from the metal surfaces of the nut and has a wire lead 226 soldered thereto to form a contact 228. The wire 226, as well as its insulating sheath 232, is encapsulated in a dielectric material 234 which may be poured into the transducer cavity to protect and insulate the transducer material 220.

The fuel line transducer herein described is usable at either end of the fuel distribution line 50, depending on accessibility. In other words, it may be used as a replacement for the retaining nut 230 at the pump or for the line retaining nut at the nozzle, as shown in FIG. 1 and FIG. 6. The operator first disconnects the retaining nut, such as the nut 230 in FIG. 8, and slides this nut up the line and out of the way. Without removing the line 50 from the outlet 214, the nut-shaped transducer housing 212 may be inserted between the nut 230 and the outlet 214 by passing the line 50 through the opening 216 cut into the side of the housing 212. The housing 212 may then be tightened onto the outlet 214 in place of the regular retaining nut 230 so as to secure the line 50 adequately to support fuel injection through the termination. As fuel is injected toward the cylinder in question from the pump 210, the line 50 tends to separate from the outlet nozzle 214 and create a stress on the transducer housing 212 which is sensed by the material 220 to generate a signal on the outlet line 226. This signal is processed or utilized by suitable circuitry as described above. For example, when the transducer shown in FIGS. 8, 8a and 8b is used in the tachometer circuit of FIG. 3 in place of the transducer 100, it provides the necessary speed-related signal for the tachometer.

From the foregoing, it is seen that there has been brought to the art in the present invention monitoring apparatus which is at the same time inexpensive and highly effective in detecting pressure changes internal to a fuel-injected cylinder. In addition, the method and apparatus disclosed herein is applicable or adaptable to a wide variety of existing injector nozzles and requires no modification of existing engine components.

While the invention has been described in connection with certain preferred embodiments, it will be understood that it is not intended that the invention be limited to those embodiments. On the contrary, we intend to cover all alternatives, modifications and equivalents as may be included within the spirit and scope of the invention as defined by the appended claims.

What is claimed is:

1. A performance monitoring system for engines having one or more cylinders adapted to receive fuel injected through a nozzle which is pressure seated into a cylinder inlet port, said system comprising holding means adapted for engaging said nozzle and maintaining pressure tending to seat said nozzle against said port, and transducer means operatively associated with said holding means for generating an electrical signal in response to changes in pressure within said cylinder.

2. The performance monitoring system of claim 1 further including output means responsive to said electrical signal to provide a visual indication of engine performance.

3. The performance monitoring system of claim 2 wherein said output means includes a tachometer circuit and meter for producing a visual indication of engine revolutions per unit of time.

4. The performance monitoring system of claim 3 wherein said transducer generates one pulse during each compression stroke of said engine and wherein said tachometer circuit includes (a) multivibrator means for producing an output pulse of constant time duration in response to each of said transducer pulses and (b) integrator means responsive to said constant duration pulses and operative to produce an output having an amplitude proportional to engine speed.

5. Apparatus for sensing forces transmitted along a fuel injector nozzle from within an engine cylinder comprising a transducer for generating an electrical signal in response to stress thereon and means for coupling said transducer to said injector nozzle such that an output signal is produced by said transducer in response to pressures acting on said nozzle from within said cylinder.

6. Apparatus according to claim 5 wherein said stress transducer includes a piezoelectric crystal.

7. Apparatus according to claim 5 further comprising a holding bracket engaging said nozzle and fastener means for coupling said holding bracket to said engine, said holding bracket being a lever-type member having first and second ends abutting said nozzle and said engine respectively and a medial portion to which said fastener means is coupled to define a pivot point, said stress transducer being mounted to said medial portion so as to detect flexing of said lever-type member at its pivot which occurs in response to pressure on said nozzle from within the cylinder.

8. Apparatus according to claim 5 further including: bracket means coupled to said nozzle and having at least one hole extending therethrough toward said engine; a transducer housing disposed adjacent to said bracket means and having an aperture therein which is coaxial with said bracket hole and a fastener extending through said hole to secure said bracket to said engine and compress said transducer housing and stress the transducer located therein in response to pressure changes within the engine cylinder.

9. Apparatus according to claim 8 wherein said transducer housing is a washer-shaped structure and wherein said transducer is a piezoelectric crystal bonded within said washer-type structure.

10. In a performance monitoring system for engines having one or more cylinders adapted to receive fuel injected through an elongated nozzle which extends into a cylinder through the engine housing, the combination comprising a bracket coupled to said nozzle, a fastener for coupling said bracket to said engine housing, said fastener being disposed so as to exert a force on said bracket which is parallel to the axis of said nozzle, and a stress transducer operatively associated with said bracket and said fastener so as to produce an output signal in response to forces acting axially on said nozzle from within said cylinder.

* * * * *